United States Patent [19]

Arrington et al.

[11] 4,215,129
[45] Jul. 29, 1980

[54] METHOD FOR THE CONTROL OF MANURE-BREEDING INSECTS

[75] Inventors: Jack P. Arrington, Clayton, Calif.; Luke L. Wade, Jackson, Tex.

[73] Assignee: The Dow Chemical Company, Midland, Mich.

[21] Appl. No.: 965,546

[22] Filed: Dec. 1, 1978

[51] Int. Cl.² .................... A01N 9/22; A01N 9/28; A61K 31/42
[52] U.S. Cl. .................................................. 424/272
[58] Field of Search ......................................... 424/272

[56] References Cited

U.S. PATENT DOCUMENTS

| 3,192,103 | 6/1965 | Sousa et al. | 424/272 |
| 3,830,914 | 8/1974 | Miller et al. | 424/219 |
| 3,957,974 | 5/1976 | Hata | 424/93 |

FOREIGN PATENT DOCUMENTS 383,985  1/1965  Switzerland ..........................424/272

Primary Examiner—V. D. Turner
Attorney, Agent, or Firm—S. Preston Jones; Ronald G. Brookens

[57] ABSTRACT

Manure-breeding insects are controlled by contacting the manure with an insecticidally-effective amount of a compound corresponding to the formula

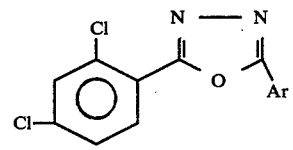

wherein Ar represents phenyl, 2-chlorophenyl, 4-fluorophenyl, 4-(trifluoromethyl)phenyl, 4-methylphenyl, 4-cyanophenyl, 2,4-dichlorophenyl or 3,5-dichlorophenyl.

4 Claims, No Drawings

METHOD FOR THE CONTROL OF MANURE-BREEDING INSECTS

BACKGROUND OF THE INVENTION

The present invention is concerned with animal husbandry and in particular, is concerned with the control of manure-breeding insects. These insects include flies which are known to be vectors in the transmission of various animal diseases.

Present control methods consist of sanitation, application of insecticides at regular intervals to control larvae or adults, bait applications, or in the case of chicken houses, even the use of flame throwers at night to kill adults resting on the ceilings and walls.

The present invention is also concerned with the use of an insecticide which can be orally administered to a warm-blooded animal and which will pass, essentially unchanged as to its insecticidal properties, through the animal's digestive system and be eliminated as a part of the animal's solid waste, i.e. manure.

The present invention is further concerned with the control of manure-breeding insects by spraying or otherwise contacting manure with an insecticide capable of controlling manure-breeding insecticides.

SUMMARY OF THE PRESENT INVENTION

The present invention is directed to a method for controlling manure-breeding insects, by spraying or otherwise contacting manure with an insecticidally-effective amount of a compound corresponding to the formula

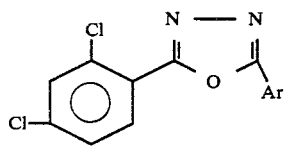

wherein Ar represents phenyl, 2-chlorophenyl, 4-fluorophenyl, 4-(trifluoromethyl)phenyl, 4-methylphenyl, 4-cyanophenyl, 2,4-dichlorophenyl or 3,5-dichlorophenyl.

The active compounds of the present invention which are utilized in the present method are highly effective in controlling manure-breeding insects such as houseflies, faceflies and hornflies. While some of the active compounds are quite effective when sprayed or otherwise admixed with the manure, some of these as well as other of the compounds have been found to be useful as feed-thru insecticides. In this latter procedure, the compound is orally administered to the animal and the compound retains its insecticidal properties after it passes through the digestive system of the treated animal. The compound when acting as a "feed-thru" mixed directly in the animal's solid waste (manure) during the digestive processes, requiring no additional work in controlling the manure-breeding insects.

In the present specification and claims, the phrase "contacting manure" and equivalent phrases thereof are employed to refer to contacting the manure (solid animal waste) outside the animal with the active material by employing techniques such as spraying, blending, and the like techniques as well as contacting manure in the animal prior to its excretion, particularly by oral administration of the active material to the animal for action in the animal as a feed-thru material.

For use as a feed-thru, the active compound can be administered to the warm-blooded animals in admixture with their feed or drinking water. Furthermore, the active compound can be administered in the form of tablets, pills, capsules or the like. The active compound can also be admixed with pharmaceutically-acceptable carriers for use in animals, however, they are usually used as a component in the animal feed or drinking water.

The insecticidally-effective dosage desirable for effective use of preparations containing the active compound will naturally depend on various factors such as the form of preparation and the insect which must be controlled. It is only necessary that the compound be orally administered in a sufficient amount so as to make possible the application of an insecticidally-effective or inactivating dosage. Generally, the active compound can be orally administered to a warm-blooded animal at a daily dosage of from about 0.25 to about 10 milligrams of active compound per kilogram of animal body weight.

When administered to poultry, an effective dosage rate will generally range from about 5 parts to about 50 parts of active compound per million parts of poultry feed.

The active compound can be effectively administered to warm-blooded animals, especially ruminants, dogs, horses, swine and poultry.

For use in direct applications to the manure, the active compound can be formulated with adjuvants into various forms, such as emulsifiable concentrates, wettable powders, dusts, oil sprays and the like. The adjuvant employed can be any one of a plurality of materials including aromatic solvents, petroleum distillates, water or other liquid carriers, surface-active dispersing agents, light absorbers and finely divided carrier solids.

The exact concentration of the active compound in composition thereof with an adjuvant therefor can vary; it is only necessary that the active compound be present in a sufficient amount so as to make possible the application of an insecticidally-effective dosage to the manure. Generally, for practical applications, the active compound can be applied to the manure in compositions containing from 0.001 percent to about 98 percent by weight of the active compound.

The present invention also comprehends the employment of compositions comprising the active compound, an adjuvant, and one or more other biologically active material such as, insecticides, fungicides, miticides, and the like.

EXAMPLES

The examples which follow should not be construed as limitations upon the overall scope of the invention.

EXAMPLE 1

A cattle feed premix containing 1.160 grams of 2,5-bis(2,4-dichlorophenyl)-1,3-4-oxadiazole was mixed into a complete cattle ration to give a total of 500 grams of completed feed. This feed was sub-divided into 100 grams samples, each containing 0.232 grams of the active compound, as the sole insecticide.

A calf weighing 232 kilograms was fed each day for 5 days, a regular feed which had been top-dressed with one of the above 100 grams samples. The active compound was present in the feed in the amount of 0.232 grams (232 mg). The feeding was observed to assure that all of the feed had been consumed.

On the fourth, fifth and sixth day of the test, manure samples were collected from the treated animal and frozen to kill any wild insect larvae that may have been present. The samples were thawed and separate samples were seeded with eggs from colony strains of hornflies or houseflies. Control samples of manure were also similarly seeded at that time. The samples were incubated at 80° F. for a period of time sufficient to allow the eggs to hatch (14 days).

The percent control was determined by counting the number of normal adult flies that hatched from the treated samples and comparing this figure with the number of flies that hatched from the untreated (control) samples. It was determined that there was, in the treated samples, a 100% kill and control of houseflies and a 82% kill and control of hornflies.

EXAMPLE 2

The compound 2,5-bis(2,4-dichlorophenyl)-1,3,4-oxadiazole was added to separate portions of commercial chicken feed in amounts sufficient to provide feeds containing from 15 to 50 parts of the compound per million parts of feed.

The feed was fed to separate groups of caged chickens of like age for 5 weeks. The chicken droppings were allowed to collect under the cages for ~one week and were allowed to become infested with the normally occurring populations of flies (i.e., houseflies). Nine-ounce sample cups were filled with the droppings and at the same time cups were filled with dropping from chickens of the same age which has been fed the same feed containing no insecticide, to serve as controls. The cups, were allowed to incubate for three weeks in separate cages until all flies had hatched and died. The dead flies were counted to determine the number of flies which hatched and compared with the number of flies which hatched from the control. The results of this test are set forth below in Table 1.

TABLE 1

| Compound | Dosage in ppm | Number of hatched flies | Percent Control of housefly hatching |
| --- | --- | --- | --- |
| 2,5-bis(2,4-dichlorophenyl)-1,3,-4-oxadiazole | 15 | 29 | 98.9 |
| | 20 | 1 | 99.9 |
| | 25 | 32 | 99.7 |
| | 30 | 170 | 93.3 |
| | 35 | 0 | 100 |
| | 40 | 8 | 99.7 |
| | 50 | 0 | 100 |
| Control | 0 | 2,524 | 0 |

EXAMPLE 3

In a similar "feed-thru" test, 2-(2,4-dichlorophenyl)-5-(3,5-dichlorophenyl)1,3,4-oxadiazole was found to give 100% kill and control of houseflies when employed at a dosage rate of 500 ppm. Likewise, 2-(2,4-dichlorophenyl)-5-(4-(trifluoromethyl)phenyl)-1,3,4-oxadiazole and 2-(2,4-dichlorophenyl)-5-(4-fluorophenyl)-1,3,4-oxadiazole each gave 100% kill and control of houseflies when employed at a dosage rate of 125 ppm.

EXAMPLE 4

Manure samples from cattle were collected and frozen to kill any wild insect larvae that may have been present. The samples were thawed and mixed with an aqueous dispersion of one of the hereinafter set forth compounds to provide a predetermined amount of the compound in the manure. The treated samples and samples containing no toxicant, to serve as controls, were each seeded with eggs from colony strains of hornflies or houseflies. The samples were incubated at 80° F. for 15 days to provide sufficient time for the eggs to hatch.

The percent control was determined by counting the number of normal adult flies that hatched from the treated samples and comparing this figure with the number of flies that hatched from the untreated (control) samples. It was determined that 2-(2,4-dichlorphenyl)-5-(4-(trifluoromethyl)phenyl-1,3,4-oxadiazole gave 100% kill and control of both hornflies and houseflies when employed at 100 ppm. Likewise 2,-(2,4-dichlorphenyl)-5-(4-fluorophenyl)-1,3,4-oxadiazole gave 100% kill and control of hornflies at 25 ppm and 100% kill and control of houseflies at 10 ppm.

Preparation of the Active Compounds

The active compounds utilized in the present method can be prepared by the reaction of an appropriate 1,3-diacylhydrazine with excess phosphoryl chloride under reflux conditions. This reaction can be characterized as follows:

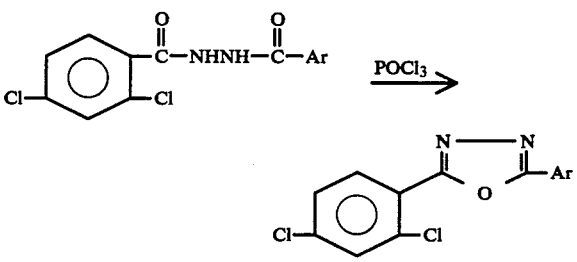

Alternatively, the active compounds can be prepared by the reaction of an appropriate carboxylic acid and hydrazine with polyphosphoric acid.

In carrying out this procedure hydrazine or its hydrate is mixed with the polyphosphoric acid and the carboxylic acid added thereto. The reaction is carried out at a temperature in the range of from about 90° to 165° C. for about 2–12 hours. After cooling to room temperature, the reaction mixture is chilled to solidify the product. The product, if desired, is washed, dried and recrystallized from a solvent such as chlorobenzene, ethanol, dioxane or mixtures thereof.

EXAMPLE 2,5-Bis(2,4-dichlorphenyl)-1,3,4-oxadiazole

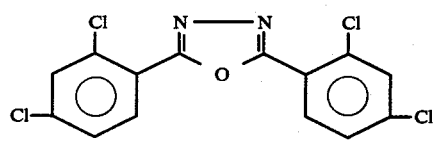

A mixture was prepared by slowly adding 10 grams (g) of hydrazine hydrate to 400 g of vigorously stirring polyphosphoric acid at ~50° C. To this mixture was added 76 g (0.4 mole) of 2,4-dichlorobenzoic acid. A slurry developed and it was stirred at 125° C (+5°) for 5 hours. The reaction products were cooled slightly and poured into ~1.5 liter (l) of cold water. The solid which precipitated was recovered by filtration, washed with water, dried and recrystallized from chlorobenzene to give 54 g (75% of theoretical) of the desired 2,5-bis(2,4-dichlorophenyl)-1,3,4-oxadiazole.

By following either of the preparative procedures outlined above:

2-(2,4-Dichlorophenyl)-5-(4-fluorophenyl)-1,3,4-oxadiazole, having a melting point of 142°–143° C.;

2-(2,Chlorophenyl)-5-(2,4-dichlorphenyl)-1,3,4-oxadiazole, having a melting point of 162°–163° C.;

2-(2,4-Dichlorophenyl)-5-(4-methylphenyl)-1,3,4-oxadiazole, having a melting point of 139°–140° C.;

2-(4-Cyanophenyl)-5-(2,4-dichlorophenyl)-1,3,4-oxadiazole, having a melting point of 208°–209.5° C.;

2-(2,4-Dichlorophenyl)-5-(4-(trifluoromethyl)-phenyl)-1,3,4-oxadiaxole, having a melting point of 146°–148° C.;

2-(2,4-Dichlorophenyl)-5-(3,5-dichlorophenyl)-1,3,4-oxadiazole, having a melting point of 201°–202° C.; and, 2-(2,4-Dichlorophenyl)-5-phenyl-1,3,4-oxadiazole, having a melting point of 121.5°–122.5° C.

What is claimed is:

1. A method for controlling manure-breeding insects which comprises contacting the manure with an insecticidally-effective amount of an active compound corresponding to the formula

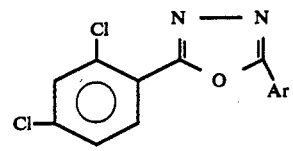

wherein Ar represents phenyl, 2-chlorophenyl, 4-fluorophenyl, 4-(trichloromethyl)phenyl, 4-methylphenyl, 4-cyanophenyl, 2,4-dichlorophenyl or 3,5-dichlorophenyl and an inert adjuvant therefor.

2. The method as defined in claim 1 wherein Ar is 2,4-dichlorophenyl.

3. The method as defined in claim 2 wherein the contacting is carried out by the oral administration of the active compound to the animal.

4. The method as defined in claim 2 wherein the excreted manure is contacted with the active compound.